(12) United States Patent
Schleipen et al.

(10) Patent No.: US 9,863,863 B2
(45) Date of Patent: Jan. 9, 2018

(54) APPARATUS FOR CLUSTER DETECTION

(71) Applicant: KONINKLIJKE PHILIPS N.V., Eindhoven (NL)

(72) Inventors: Johannes Joseph Hubertina Barbara Schleipen, Eindhoven (NL); Menno Willem Jose Prins, Rosmalen (NL); Andrea Ranzoni, Voghera (IT)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 76 days.

(21) Appl. No.: 14/357,790

(22) PCT Filed: Nov. 6, 2012

(86) PCT No.: PCT/IB2012/056186
§ 371 (c)(1),
(2) Date: May 13, 2014

(87) PCT Pub. No.: WO2013/072806
PCT Pub. Date: May 23, 2013

(65) Prior Publication Data
US 2014/0302619 A1    Oct. 9, 2014

Related U.S. Application Data

(60) Provisional application No. 61/559,307, filed on Nov. 14, 2011.

(51) Int. Cl.
*G01N 3/38* (2006.01)
*G01N 27/72* (2006.01)
(Continued)

(52) U.S. Cl.
CPC ......... *G01N 15/14* (2013.01); *G01N 21/0303* (2013.01); *G01N 21/51* (2013.01);
(Continued)

(58) Field of Classification Search
CPC .... G01N 15/14; G01N 21/0303; G01N 21/51; G01N 21/6452; G01N 21/6486;
(Continued)

(56) References Cited

U.S. PATENT DOCUMENTS 8,217,647 B2    7/2012  Dittmer
8,981,772 B2    3/2015  Ranzoni
(Continued)

FOREIGN PATENT DOCUMENTS

JP            8075639 A      3/1996
WO       2008102218 A1      6/2007
(Continued)

OTHER PUBLICATIONS

Paivo Kinnunen, "High frequency asynchronous magnetic bead rotation for improved biosensors", Applied Physics Letters, AIP, American Institute of Physics, Melville, NY 97, No. 22, Nov. 29m, 2010, pp. 223701-223701.
(Continued)

*Primary Examiner* — Robert Eom

(57) ABSTRACT

The invention relates to a sensor apparatus (100) and a method for detecting clusters with magnetic particles in a sample. The sample is provided in at least one sample chamber (114) of a substantially planar cartridge (110) that is exposed to a modulated magnetic field ($B_{xz}$, $B_{yz}$) generated by a magnetic field generator (190). The sample chamber (114) is illuminated with excitation light ($L_0$), and the resulting output light ($L_s$) is detected by a light detector (180). The magnetic field ($B_{xz}$, $B_{yz}$) may particularly rotate, inducing a corresponding rotation of clusters which in turn induces a variation of the detection signal (S). According to a preferred embodiment, excitation light ($L_0$) is focused onto blocking spots (173) behind the sample chamber (114), thus shielding the light detector (180) from direct illumination.

15 Claims, 4 Drawing Sheets

(51) Int. Cl.

| | |
|---|---|
| *G01N 15/14* | (2006.01) |
| *G01N 21/03* | (2006.01) |
| *G01N 21/51* | (2006.01) |
| *G01N 21/64* | (2006.01) |
| *G01N 33/543* | (2006.01) |
| G01N 21/25 | (2006.01) |
| G01N 21/17 | (2006.01) |

(52) U.S. Cl.
CPC ..... *G01N 21/6452* (2013.01); *G01N 21/6486* (2013.01); *G01N 27/72* (2013.01); *G01N 33/54326* (2013.01); *G01N 33/54373* (2013.01); *G01N 21/253* (2013.01); *G01N 21/6454* (2013.01); *G01N 2021/1727* (2013.01)

(58) Field of Classification Search
CPC .. G01N 21/253; G01N 21/6454; G01N 27/72; G01N 33/54326; G01N 33/54373; G01N 2021/1727
See application file for complete search history.

(56) References Cited

U.S. PATENT DOCUMENTS

| | | | |
|---|---|---|---|
| 2007/0146701 A1 | 6/2007 | Kiesel | |
| 2008/0220411 A1* | 9/2008 | McNaughton | ... G01N 33/54313 435/5 |
| 2009/0238514 A1 | 9/2009 | Hu | |
| 2010/0322824 A1 | 12/2010 | Neijzen | |
| 2011/0053290 A1 | 3/2011 | Ahn et al. | |
| 2011/0199080 A1 | 8/2011 | Ovsyanko | |
| 2012/0003750 A1 | 1/2012 | Ranzoni | |
| 2013/0114076 A1 | 5/2013 | Schleipen | |
| 2014/0120632 A1 | 5/2014 | Ranzoni | |
| 2014/0127722 A1 | 5/2014 | Ranzoni | |

FOREIGN PATENT DOCUMENTS

| | | |
|---|---|---|
| WO | 2008112626 A1 | 9/2008 |
| WO | 2009066236 A1 | 5/2009 |
| WO | 2009074933 A1 | 6/2009 |

OTHER PUBLICATIONS

X.J.A. Janssen et al, "The rotating particles probe: A new technique to measure interactions between particles and a substrate", Colloids and Surfaces A: Physicochemical and Engineering Aspects 373, pp. 88-93 (2011).

A. Ranzoni et al, "Frequency-Selective Rotation of Two-Particle Nanoactuators for Rapid and Sensitive Detection of Biomolecules", NANO Letters, Nov. 2011, 2017-2022.

Anil Vuppu et al, "Phase sensitive enhance for biochemical detection using rotating paramagnetic particle chains", Journal of Applied Physics, American Institute of Physics, NY, US, vol. 96, No. 11, Jan. 1, 2004, pp. 6831-68-38.

Irene Sinn et al, "Asynchronous magnetic bead rotation (AMBR) biosensor in microfluidic droplets for rapid bacterial growth and susceptibility measurements", Lab on a Chip, vol. 11, No. 15, Jan. 1, 2011, p. 2604.

Park, Sang Yoon et al "Magneto-Optical Biosensing Platform Based on Light Scattering from Self-Assembled Chains of Functionalized Rotating Magnetic Beads", Nano Letters, vol. 10, No. 2, 2010, pp. 446.

Baudry, J. et al "Acceleration of the recognition rate between grafted ligands and receptors with magnetic forces", PNAS, vol. 103, No. 44, 2006, pp. 16076-16078.

Koh, Isaac et al "Sensitive NMR Sensors Detect Antibodies to Influenza", Angew Chem Int Ed. Engl. vol. 47, No. 22, 2008, pp. 4119-4121.

Moser, Y. et al "On-chip immuno-agglutination assay with analyte capture by dynamic manipulation of superparamagnetic beads", Lap Chip, vol. 9, 2009, pp. 3261-3267.

* cited by examiner

APPARATUS FOR CLUSTER DETECTION

CROSS-REFERENCE TO PRIOR APPLICATIONS

This application is the U.S. National Phase application under 35 U.S.C. §371 of International Application No. PCT/IB2012/056186, filed on Nov. 6, 2012, which claims the benefit of U.S. Provisional Patent Application No. 61/559,307, filed on Nov. 14, 2011. These applications are hereby incorporated by reference herein.

FIELD OF THE INVENTION

The invention relates to a sensor apparatus and a method for detecting clusters comprising magnetic particles in a sample. Moreover, it relates to a cartridge for such an apparatus.

BACKGROUND OF THE INVENTION

The detection of clusters comprising magnetic particles by rotating them and detecting the light scattered in a dark field configuration is known from literature (Ranzoni, A., Schleipen, J. J. H. B., van Ijzendoorn, L. J. & Prins, M. W., "Frequency-Selective Rotation of Two-Particle Nanoactuators for Rapid and Sensitive Detection of Biomolecules", Nano Lett 11, 2017-2022). In the described setup, a sample with the clusters is provided in a cuvette.

SUMMARY OF THE INVENTION

It is an object of the invention to provide means that allow for the application of cluster detection in a clinical environment, particular in a handheld, miniaturized biosensor platform.

This object is achieved by a sensor apparatus according to claims 1 and 2, a method according to claim 3, and a cartridge according to claim 13. Preferred embodiments are disclosed in the dependent claims.

According to a first aspect, the invention relates to a sensor apparatus for detecting in a sample clusters comprising magnetic particles. In this context, the term "magnetic particle" shall comprise both permanently magnetic particles as well as magnetizable particles, for example superparamagnetic beads. The size of the magnetic particles typically ranges between 3 nm and 50 µm. The considered "clusters" are agglomerates of two or more particles (at least one of them being magnetic) which are coupled by some kind of binding. Of particular interest are specific (biochemical) bindings via special chemical groups and intermediate components of interest and, in contrast thereto, nonspecific bindings that are e.g. merely caused by magnetic attraction forces between magnetized particles. The sensor apparatus comprises the following components:

a) A cartridge with at least one sample chamber in which the sample can be provided. The cartridge shall preferably be substantially planar, the extension of the cartridge defining a "cartridge-plane" that will be referred to below.

In this context, a cartridge is considered as being "substantially planar" if its length and width (extension in x- and y-direction of a rectangular coordinate system) are more than about 3-times, preferably more than about 10-times larger than its height (extension in z-direction). Moreover, the outer surfaces of a "planar cartridge" will usually be flat and/or without protrusions.

The cartridge will usually be an exchangeable component and/or a disposable component which is used only once for a single sample. It will preferably be at least partially transparent. The "sample chamber" is typically an open cavity, a closed cavity, or a cavity connected to other cavities by fluid connection channels. Moreover, it is preferred that a plurality of such sample chambers is provided to allow for the parallel execution of assays with one or more samples.

b) A light source for emitting light into the aforementioned at least one sample chamber, wherein said light will in the following be called "excitation light" for the purpose of reference. The light source may for example be a laser or a light emitting diode (LED), optionally provided with some optics for shaping and directing the excitation light beam.

c) A magnetic field generator for generating a modulated (i.e. time-variable) magnetic field in the sample chamber. The magnetic field will usually be such that it induces a correspondingly modulated movement of clusters comprising magnetic particles. The magnetic field generator may particularly be realized by permanent magnets or electromagnets.

d) A light detector for detecting light that was generated by the excitation light in the sample chamber, wherein said light will in the following be called "output light" for the purpose of reference. The output light may particularly comprise light that was generated by the scattering of excitation light by clusters and/or fluorescence light of fluorescent clusters that were excited by the excitation light.

According to a second aspect, the invention relates to a method for detecting clusters comprising magnetic particles in a sample, said method comprising the following steps that may be executed in the listed or any other appropriate order:

a) Introducing the sample, the assay reagents including magnetic particles, and clusters to be detected into the at least one sample chamber of a substantially planar cartridge.

b) Emitting excitation light into said sample chamber.

c) Generating a modulated magnetic field in the sample chamber.

d) Detecting output light that was generated by the excitation light in the sample chamber.

The sensor apparatus and the method are different realizations of the same inventive concept, i.e. the detection of clusters comprising magnetic particles in a planar cartridge. Explanations and definitions provided for one of these realizations are therefore valid for the other realization, too. The sensor apparatus and the method have the advantage that they allow for the execution of cluster assays in a clinical environment because medical samples can be examined in a substantially planar cartridge. The form of this cartridge enables the usage of small sample volumes because the required sensor components can be brought close to the sample.

In the following, various preferred embodiments of the invention will be described that relate to the sensor apparatus and the method described above.

The light detector is preferably disposed adjacent to the plane of the cartridge, i.e. to the plane defined by the planar extension of the cartridge. To put it differently, the light detector is not disposed in the same plane as the cartridge. Most preferably, the light detector is additionally disposed adjacent to the cartridge itself (not only adjacent to the— infinitely extending—plane of the cartridge). In this way it can be guaranteed that there is a short distance between the sample chamber and the light detector, thus minimizing any losses of output light. The light detector may especially be disposed perpendicularly above the sample chamber with respect to the cartridge-plane.

In general, the modulation of the magnetic field in the sample chamber may have any arbitrary temporal course. Preferably, the modulation of the magnetic field is periodic, thus providing a characteristic frequency that may be recovered in the output light. In a preferred embodiment, the magnetic field rotates (i.e. at least one component of the field vector rotates in a given plane). Such a rotation typically induces a corresponding rotation of magnetic clusters.

Moreover, the magnetic field may (additionally or alternatively) be at least once interrupted by a pause, wherein the duration of the pause preferably ranges between about 0.01 s and about 10 s, most preferably between about 0.1 s and about 5 s. The magnetic field may particularly be pulsed, i.e. periodically switched on and off. The pulse frequency may preferably range between about 0.1 Hz and 100 Hz.

The plane in which the magnetic field (or a component thereof) rotates preferably comprises the (main or average) direction of propagation of the excitation light and/or of the output light. This implies that the excitation light or the output light, respectively, "sees" a time-variable cross section of non-spherical clusters that are rotated by the magnetic field in said plane. Accordingly, the interaction between the clusters and the excitation light or the output light will be modulated, too.

According to another embodiment of the invention, an evaluation unit is provided for evaluating the detector signals that are generated by the light detector, particularly for evaluating them with respect to their temporal spectrum (i.e. at least a part of their temporal spectrum is determined). This allows to identify spectral signal components that are related to the modulation of the magnetic field and thus to clusters actuated by this field. A magnetic field rotating with a given frequency will for example induce, via the clusters, components in the detector signal at this frequency or higher harmonics thereof.

There are different ways how the illumination of the sample chamber with excitation light can be achieved. According to one embodiment, a nontransparent blocking spot is provided between the sample chamber and the light detector, wherein the excitation light is focused onto said blocking spot. Accordingly, the excitation light can pass through the sample chamber (which is in front of the blocking spot) but cannot reach the light detector (which is behind the blocking spot). This has the advantage that the measurement of the light detector is shielded from a high background signal produced by a direct illumination with excitation light. At the same time, the directions of excitation light and output light can substantially be parallel, which allows an arrangement of the associated optical components adjacent to the cartridge-plane. The blocking spot may for example be disposed on a separate optical carrier or on a lens.

The aforementioned nontransparent blocking spot may simply comprise a material that absorbs the excitation light. In a preferred embodiment, the blocking spot may be reflective. Excitation light can then be reflected back into the sample chamber, thus preventing its loss.

The output light will usually be divergent as it is generated by random processes like scattering. If the light detector can be placed close enough to the sample chamber and if it is large enough, it may be capable of directly capturing a sufficient amount of (divergent) output light. In another embodiment, optical elements may be disposed between the sample chamber and the light detector for directing and/or focusing output light onto the light detector by reflection, refraction, or diffraction.

The light source may be disposed adjacent to the plane of the cartridge (preferably adjacent to the cartridge itself) for illuminating the sample chamber from a direction substantially perpendicular to the cartridge-plane. In this case, the light detector may be arranged opposite to the light source with respect to the cartridge-plane. In another embodiment, the light source and the light detector are disposed on the same side of the cartridge-plane, which leaves room on the opposite side of the cartridge-plane for other (e.g. fluidic) components of the apparatus. A "distribution element" may in this case be provided for directing excitation light that propagates parallel to the cartridge-plane into the sample chamber. The light source can then be disposed lateral of the light detector, its excitation light first propagating along the cartridge-plane until it reaches the position of the sample chamber where it is directed by the distribution element into said chamber.

According to a further development of the aforementioned embodiment, the distribution element comprises at least one "partial mirror", i.e. a mirror which reflects incident light but also allows the passage of incident light. The percentages of reflected and transmitted incident light may depend on the properties of said light, for example its color or polarization. The partial mirror may for example completely (100%) reflect incident excitation light of a first color and allow the complete passage (0% reflection) of incident output (e.g. fluorescence) light having another color. With the partial mirror, excitation light can be redirected into the sample chamber and output light coming from the sample chamber can at the same time be passed on to the light detector (or vice versa).

If the partial mirror has some transparency for excitation light, a plurality of sample chambers can be illuminated in parallel. This is because excitation light that has passed a first partial mirror can be directed into a second sample chamber by a second partial mirror, and so on. With a series of partial mirrors, a plurality of sample chambers can hence be illuminated by one excitation light beam propagating initially parallel to the cartridge-plane. The partial mirrors may optionally have different transparencies for the excitation light, thus controlling the amount of excitation light each sample chamber receives.

It was already mentioned that the output light may (at least partially) be generated by scattering of excitation light. According to another embodiment, the output light may comprise light that was generated by fluorescence of fluorescent clusters when being excited by excitation light. The emission of fluorescence light from a cluster may be anisotropic such that an induced movement of the cluster may be detected by a variation of the observed fluorescence. Moreover, an induced movement of clusters may expose varying cross sections to the excitation light, thus implying a time-variable excitation of fluorescence.

According to a further development of the aforementioned embodiment, a filter element is provided between the sample chamber and the light detector for spectrally filtering out excitation light while allowing the passage of output light. Thus the light detector can be shielded from a high background signal of direct excitation light, which comprises no information about clusters.

The invention further relates to a cartridge that is particularly designed for a usage in a sensor apparatus or a method according to the invention, wherein said cartridge is however a standalone component (and commodity) of its own. The cartridge comprises the following components:

a) A transparent layer in which at least one sample chamber is formed and through which excitation light can propagate.

b) An "additional layer" that is disposed adjacent to the aforementioned transparent layer and at which excitation light is reflected.

If the additional layer shows a specular reflection, it can reflect light that wants to leave the sample chamber back into the chamber, thus preventing its loss. Such an embodiment can particularly be used if the light source and the light detector are disposed on the same side of the cartridge.

According to a further development of the cartridge, the transparent layer is disposed between two additional layers at which the excitation light is reflected, wherein said additional layers have lower refractive indices than the transparent layer. Excitation light propagating within the transparent layer may then be totally internally reflected at the additional layers, making the transparent layer act as a waveguide for the excitation light. This allows for an efficient side illumination of the sample chamber(s) in the additional layer.

BRIEF DESCRIPTION OF THE DRAWINGS

These and other aspects of the invention will be apparent from and elucidated with reference to the embodiments described hereinafter.

In the drawings.

Like reference numbers or numbers differing by integer multiples of 100 refer in the Figures to identical or similar components.

DETAILED DESCRIPTION OF EMBODIMENTS

The US 2010/0322824 A1 describes a point-of-care biosensor (also called Philips "MagnoTech" platform) based on magnetic particles and optical detection. Particles coated with capture molecules (e.g. antibodies) are used for capture of biomarkers and subsequent detection. The advantage of using magnetic particles is that they can be actuated by magnetic fields, which enhances the speed of the biosensor and avoids the need for complicated fluid manipulations in an integrated biosensor cartridge. The described technology is based on the binding of magnetic particles to a sensor surface and detection of the particles by Frustrated Total Internal Reflection (FTIR).

An alternative way to perform a biological assay is in a so-called cluster assay. Cluster/agglutination/aggregation assays are based on a biologically or biochemically induced aggregation or clustering of particles, which indicates the presence and/or concentration of a biological moiety, called the target or the biomarker. In a standard protocol, the particles bind to the target and, by waiting a longer time, target-linked clusters are formed. The tests may be performed in microwells, aggregation can be read by eye or by an instrument, and the amount of clustering is correlated with the concentration of target in the sample. Agglutination assays are generally qualitative and not very sensitive. However thanks to their simple assay format, they are cost-effective.

A particular type of cluster assays is based on the use of magnetic particles. The advantage is that a magnetically induced arrangement of particles in chains can be applied, which results in a rapid formation of target-induced clusters (Baudry et al., PNAS vol. 103, p. 16076, 2006). Several detection techniques have been described, all having the disadvantage that they measure small relative changes of a physical property of the clusters and are hindered by the presence of a large baseline signal. Another factor that hinders the technology to find commercial applications is the occurrence of non-specific particle clustering, particularly in matrices of complex biological composition.

Figure 1:
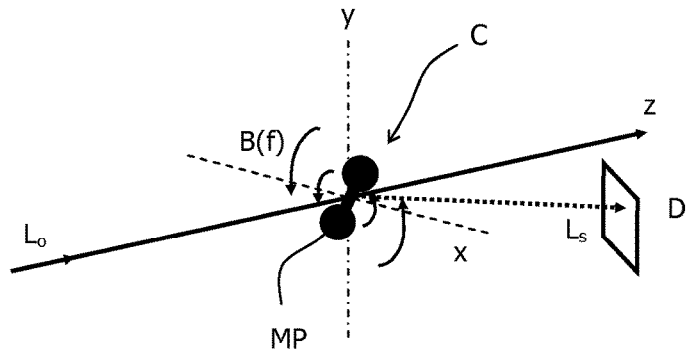
FIG. 1 schematically shows the detection of light scattered by a rotating cluster of two magnetic particles.

FIG. 1 illustrates a novel detection technique based on magnetically controlled rotation of the particle clusters and the detection of scattered light in a dark-field configuration (Ranzoni et al., above). In a cuvette (not shown) clusters C of magnetic nanoparticles MP are being formed as a result of biochemical interactions between nanoparticles. The sample volume is excited by a beam $L_0$ of light directed along the z-axis, giving rise to scattering of light $L_s$ when the input light beam impinges onto the nanoparticles. The scattered light $L_s$ may be detected by a light detector D.

Upon the application of a rotating external magnetic field B(f) (rotating in the yz-plane with frequency f), the clusters C start rotating in the magnetic field and generate a modulation of the light scattering $L_s$. The actuation and detection scheme allows a discrimination of clusters from single particles in solution. Specific binding in clusters can be enhanced for example by the application of a pulsed magnetic chaining field, and non-specific particle clustering in complex matrices can be reduced by means of dedicated surface chemistries, e.g. a double-layered molecular architecture on the particles.

If the detection principle of FIG. 1 shall become suitable for point-of-care applications, a cartridge technology and readout technology is needed that preferably fulfils the following requirements:

1. The cartridge and reader should be reliable and easy to use. The cartridge should be disposable and cost-effective. The cartridge should be able to integrate several functions, e.g. sample filtration, reagent release into the sample, incubation, detection, etc. The reader should be compact and cost-effective.

2. The cartridges and readout system should be suited for multiple assay chambers in order to allow for assay multiplexing. Preferably the technology should be scalable, making it easy to change the number of assay chambers in the cartridge.

3. Preferably the system should be suited for small sample volumes, e.g. a finger-prick sample of blood. Preferred sample volumes are ranging from 100 µl down to volumes much lower than 1 µl. The sample may be split over the one or more reaction chambers in the cartridge.

4. Detection needs to be sensitive and the highest possible signal should be gathered from every magnetic cluster present in a detection chamber. This means that the optical system should effectively probe the magnetic particles in every chamber.

5. The cartridge technology should be compatible with the presence of an electromagnetic system for the application of dynamic magnetic fields to the magnetic particles.

In order to address all the mentioned issues, a system with a cartridge and a reader is proposed, with:
- a cartridge with an essentially planar architecture with at least one sample chamber (reaction chamber),
- a reader instrument with an arrangement for magnetic actuation of clusters of magnetic particles in the at least one sample chamber,
- an optical arrangement to optically excite the magnetic particles in the at least one sample chamber,
- an optical detection arrangement to detect light scattered from the magnetic particles in the at least one sample chamber, wherein the axis of the optical detection is preferably essentially parallel to the cartridge normal (i.e. perpendicular to the cartridge-plane).

For sensitive detection the scattered light should be detected with high efficiency. Preferably the excitation light does not directly reach the optical detector, so as to achieve a dark-field measurement. It should however be noted that dark-field detection is not strictly necessary, since the signal from the dynamically actuated clusters is obtained by appropriate spectral filtering (in the temporal domain), thereby filtering out any scattered or reflected light from the excitation beam. However, if the DC-like contribution from the direct scattered or reflected excitation light is becoming too large, this may lead to a decreased signal-to-noise ratio and a decreased dynamic range of the rotating cluster signal. Therefore dark-field detection is preferred since it will lead to a better SNR and larger dynamic range.

Moreover, it should be noted that the term "dark-field" may equally well be used for the following two situations:
(1) Optical dark-field detection using spatial filtering in the optical domain.
(2) Optical bright-field detection using appropriate spectral filtering in the electronic domain.

Preferably the numerical aperture $NA_{det}$ of the detection optics should be as high as possible in order to guarantee a high detection efficiency. Given a certain sample chamber geometry with a spacing between two neighboring sample chambers of D, and detection optics with a certain focal length of $f_{det}$, the numerical aperture is limited by $NA_{det} < D/2f_{det}$, or the sample chamber spacing should be chosen such that $D > 2 \cdot f_{det} \cdot NA_{det}$.

Although high numerical apertures may be achieved and used, the system is inherently insensitive to optical disturbances like scratches, fingerprints or dust on cartridges or reader optics, since these disturbances lead to a steady, DC-like signal deterioration, which is being filtered out by a phase sensitive detection scheme (i.e. filtering in Fourier-frequency domain).

Figure 2:
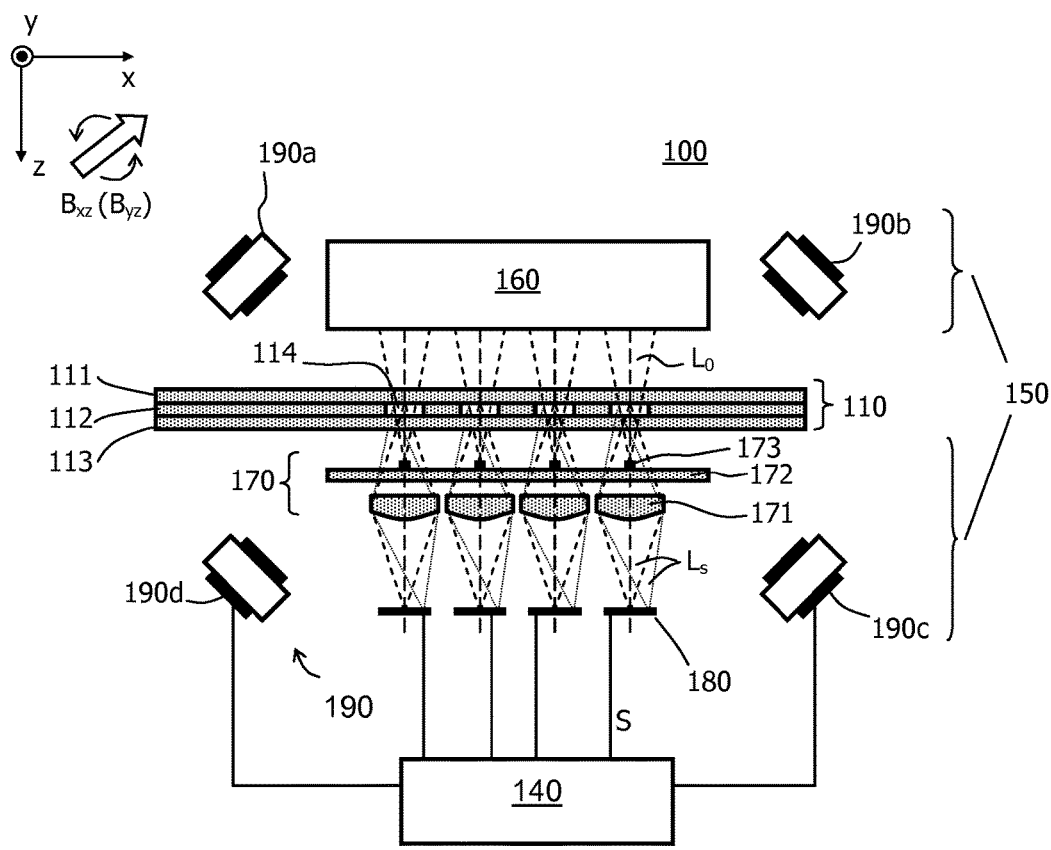
FIG. 2 shows a sensor apparatus in which light source and light detector are disposed on opposite sides of the cartridge-plane with blocking spots on a carrier.

In FIG. 2 a first embodiment of a sensor apparatus 100 is shown that is designed according to the above principles and capable of doing dark-field detection of rotating clusters in a planar cartridge 110, detecting multiple sample chambers 114 at the same time. The cartridge 110 consists of:
- a transparent bottom substrate 113;
- a transparent top substrate 111;
- an intermediate layer 112 containing a multitude of sample chambers 114.

Intermediate layer 112 and more specifically the sample chambers 114 may also be part of the top and/or bottom layers 111, 113 by using techniques like embossing or injection molding. Also the micro fluidics (not shown) required for bringing the sample fluid to the sample chambers 114 may either be part of the intermediate layer 112, or it may be made directly in top and/or bottom layers 111, 113.

The cartridge 110 is inserted in a readout system or "reader" 150, comprising:
- A light source 160, i.e. an optical arrangement for making a series of converging beams of "excitation light" $L_0$, the individual convergent beams illuminating the sample chambers 114.
- A transparent substrate 172 containing small opaque or reflecting areas, called "blocking spots" 173 in the following, positioned in the foci of excitation light beams, thereby blocking the excitation light and preventing it from hitting and saturating the detector. If the blocking spots 173 are reflecting, the excitation light $L_0$ is directed towards the sample chamber again, resulting in a factor two more signal.
- An array of light detectors 180 for detecting "output light" $L_s$ that is generated in the corresponding sample chambers 114. Each light detector 180 may be a single Si-detector or (part of) a 2D array like a CCD or CMOS sensor. Since the method relies on a bulk sample measurement, imaging and planar resolution are not required, and the use of a single detector is preferred (because of cost and signal-to-noise aspects).
- An evaluation unit 140, for example a digital data processing unit, for processing and evaluating the detection signals S provided by the light detectors 180.
- A magnetic field generator 190, here realized by four electromagnets 190a, 190b, 190c, and 190d in a quadrupole arrangement.

The detector signal S of each light detector 180 is derived from the scattered output light $L_s$ originating from the corresponding sample chamber 114. This scattered light $L_s$ is collected by a lens 171 disposed between the sample chamber 114 and the light detector 180 and focused on the detector 180.

For multiplexing a (one- or two-dimensional) array of sample chambers 114 is needed, and the full embodiment consists of an array of associated light sources, blocking spots 173, lenses 171, and light detectors 180. Precautions should be taken such that scattered output light $L_s$ arising from one chamber is not detected by the detection optics of another chamber in order to prevent optical cross talk between the different chambers 114.

Also part of the reader 150 is the magnet arrangement 190 creating a modulated magnetic field. Preferably, this is a magnetic field $B_{xz}$ rotating in the xz-plane, or a magnetic field $B_{yz}$ rotating in the yz-plane (or a combination thereof). In both cases, the rotation of the magnetic field is in a plane containing the excitation beam $L_0$ (which is directed along the z-axis).

The detector signal S from each light detector 180 is subsequently spectrally filtered in the evaluation unit 140 such that only the contribution from the rotating clusters is obtained, thereby filtering out the DC-content originating from e.g. single nanoparticles, scratches, etc.

FIGS. 3-7 show various modifications of the sensor apparatus and cartridge of FIG. 2, wherein identical or similar components have reference signs differing by integer multiples of 100 and will not be explained again. It should be noted that the magnetic field detector 190 and the evaluation unit 140 are not shown in these drawings, though they are always part of the setup.

Figure 3:
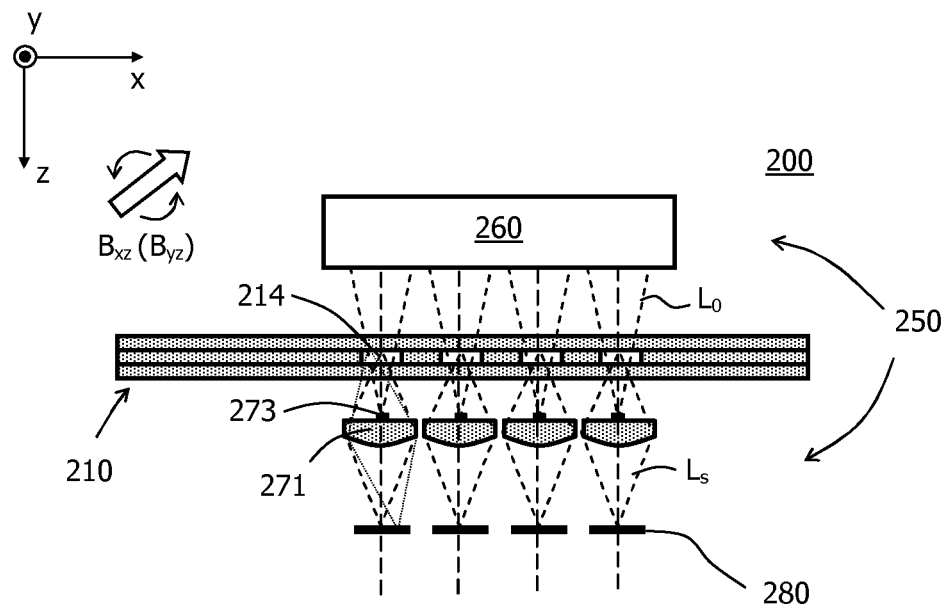
FIG. 3 shows a modification of the sensor apparatus of FIG. 2 in which the blocking spots are disposed directly on lenses.

FIG. 3 illustrates a second embodiment of a sensor apparatus 200 for dark-field detection of cluster-assays. In contrast to the sensor apparatus of FIG. 2, the blocking spots 273, allowing dark-field detection, are now part of the lenses 271. A reflecting or absorbing spot 273 can be made directly on top of a lens 271 by standard thin-layer deposition techniques.

Furthermore, the collection of discrete lenses 271 may be replaced by a single component like a lens array, made via standard techniques like injection molding, 2P-replication or glass molding. The advantage of using a lens array with fixed distances between the discrete lenses is in the alignment of the optical system during fabrication. In this case the distance between the individual light sources generating the excitation beams $L_0$, between the individual lenses 271, and between the individual detectors 280 is fixed and is determined by the distance between the individual sample chambers 214.

Figure 4:
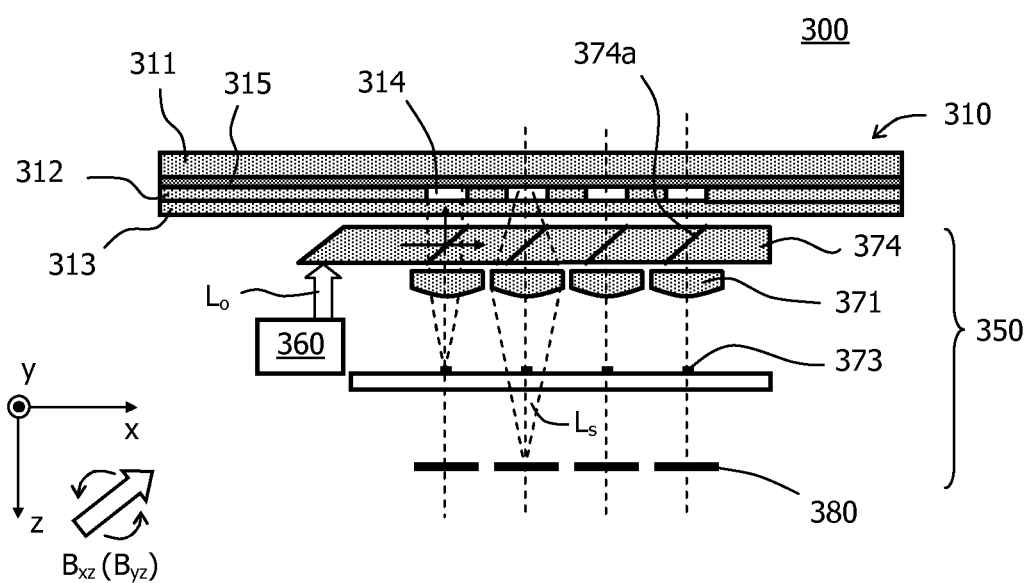
FIG. 4 shows a sensor apparatus in which light source and light detector are disposed on the same side of the cartridge, wherein excitation light is directed into the sample chambers by a distribution element.

FIG. 4 shows a third embodiment of a sensor apparatus 300 for dark-field detection of cluster-assays where the excitation optics and the detection optics are located at only one side of the cartridge 310. Advantages of this geometry are (i) the use of only one optically transparent (bottom) substrate 313, and (ii) the realization of a thin, planar readout system where all optics is located at only one side of the cartridge.

Just underneath the cartridge 310 an optical arrangement or "distribution element" 374 is positioned distributing the incoming excitation light beam $L_0$ over the different sample chambers 314. The distribution element 374 may be comprised of a single waveguiding optical component containing partially reflecting, polarizing or non-polarizing beam splitting mirrors 374a. Here, also discrete optics may be used in order to couple in light into the cartridge 310. The reflection coefficients of the individual mirrors 374a may be carefully chosen such that the overall intensity of the light reaching the individual sample chambers 314 is the same for all chambers. In order to prevent stray light from the excitation beam $L_0$ hitting the detector 380, either (i) the light should be fully absorbed when it hits the upper cartridge layer 311, or (ii) the light hits another intermediate "additional layer" 315 that is fully reflecting the light towards an absorbing or reflecting blocking element 373, in the same way as described above, and thereby allowing dark-field detection of the scattered light.

Figure 5:
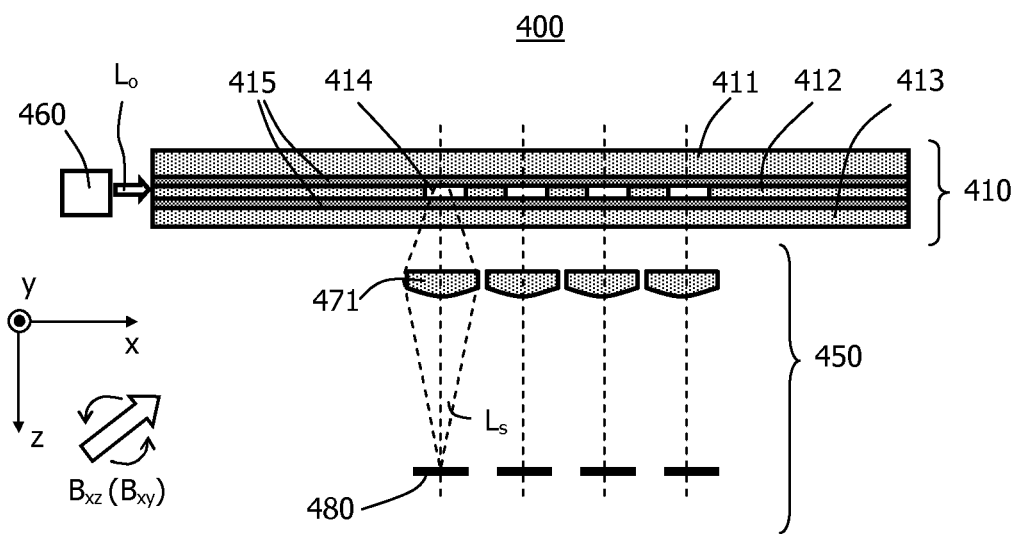
FIG. 5 shows a sensor apparatus in which a transparent layer functioning as a waveguide is illuminated from the side.

FIG. 5 shows a fourth embodiment of a sensor apparatus 400 for dark-field detection of cluster-assays with side-way excitation. Here, the excitation light $L_0$ is coupled into a transparent guiding layer 412 of the cartridge 410 containing the sample chambers 414. Optical arrangements in order to couple in light from a light source 460 into a waveguiding component are well known in prior art, such as (i) butt coupling using a lens with an appropriate NA, focusing the light at the side of the cartridge 410, (ii) using planar diffracting or refracting structures at the top of the underlying layers 411, 413.

In order to have the transparent layer 412 of the cartridge 410 act as an optical waveguide, the different layers 411, 412, and 413 of the cartridge should be interconnected using intermediate "additional layers" 415 with a refractive index lower than that of the guiding layer 412, e.g. using optical glues with a low refractive index.

Since the main direction of propagation of the excitation light $L_0$ is now the x-direction (detection still in the z-direction), this implies that (i) the scattered light $L_s$ is now collected at right angles with respect to the excitation beam $L_0$, and (ii) the orientation of the plane of the rotating magnetic field ($B_{xz}$ or $B_{xy}$) is now preferably in the xz- and/or xy-direction.

Figure 6:
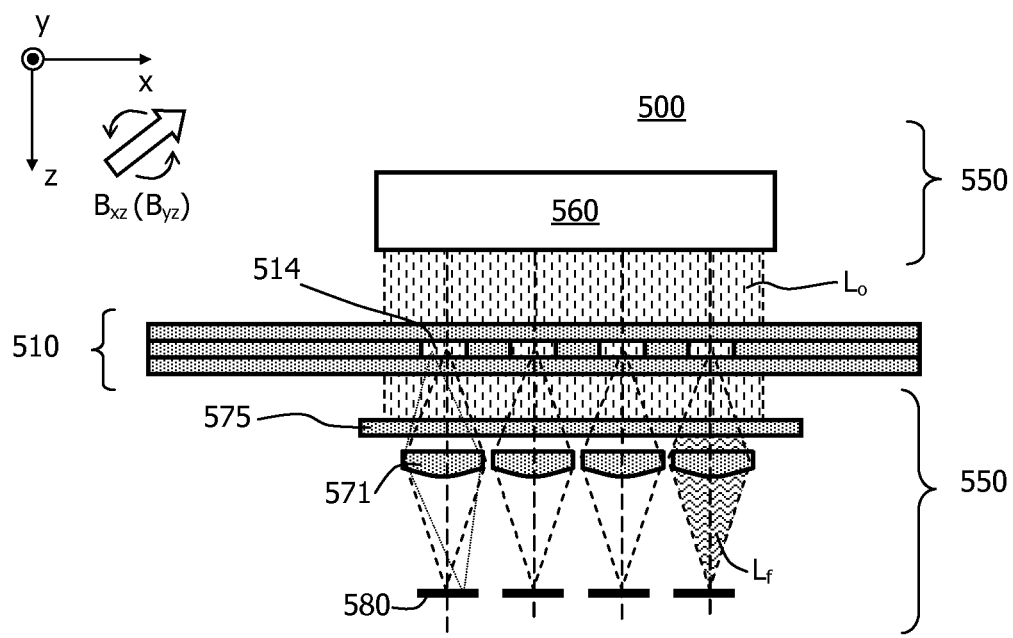
FIG. 6 shows a sensor apparatus in which fluorescence of magnetically actuated clusters is observed.

FIG. 6 shows a fifth embodiment of a sensor apparatus 500 for dark field detection using fluorescently labeled magnetic nanoparticles. Dark field detection can also be obtained in the spectral (i.e. wavelength) optical domain by using fluorescently labeled magnetic nanoparticles. In this case, since direct stray light from the excitation light beam $L_0$ is prevented from hitting the light detector 580 by an appropriate optical filter 575 between the sample chambers 514 and the light detectors 580, the excitation optics becomes very simple: the cartridge 510 as a whole may now be illuminated, for example by a single light source 560 with a uniform beam of light $L_0$. It should be noted that this illumination may also be done from the bottom (as in FIG. 4) or from the side (FIG. 5).

The role of the blocking spots has now been replaced by the spectral (wavelength) filter 575, filtering out the excitation wavelength and preventing the detector to become saturated by the high intense excitation beam. Only fluorescence output light $L_f$ can reach the detectors 580. A second filtering step then occurs in the spectral (time) domain, whereby only the e.g. 2f-component of the detector signal is detected and is accounting for the concentration of analytes present in the bulk sample fluid (wherein f is the frequency of rotation of the rotating magnetic field).

Due to the absence of a spatial filter (blocking elements) the detection optics also may become much simpler and the reader might be constructed without additional lenses 571 by placing the detector as close to the cartridge as possible.

Figure 7:
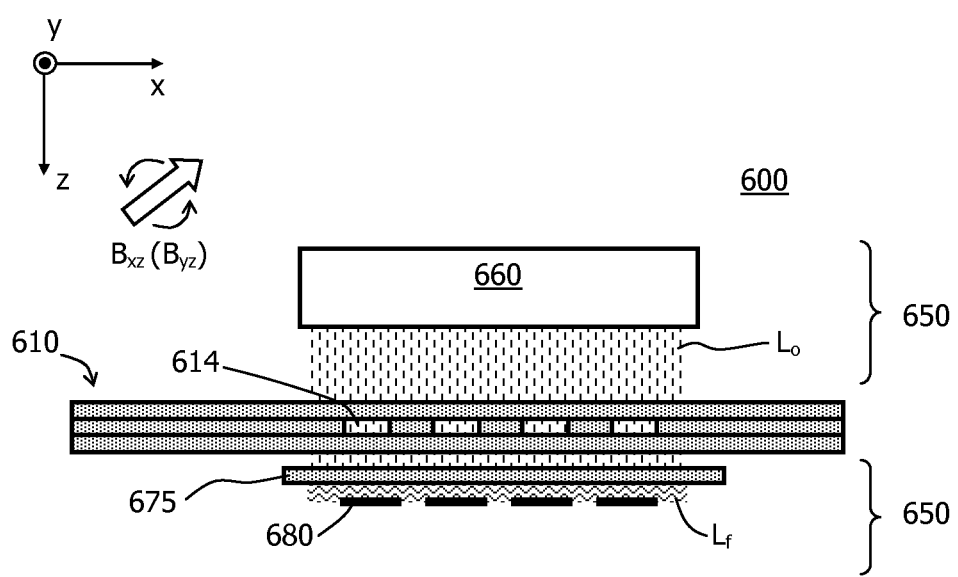
FIG. 7 shows a modification of the sensor apparatus of FIG. 6 in which no optics is used in front of the light detector.

A corresponding embodiment of a sensor apparatus 600 using fluorescently labeled magnetic nanoparticles is shown in FIG. 7. By using detectors 680 with a footprint in the order of the area of the sample chambers 614, the amount of collected fluorescence output light $L_f$ can be maximized without the use of lenses. In this case a very compact and ultra-thin reader device 650 is obtained. While this is illustrated in FIG. 7 with the excitation beam $L_0$ coming from above, also here the excitation beam might equally well come from below, or from the side of the cartridge 610.

The use of fluorescence has the advantage of eliminating the need of preventing the excitation beam $L_0$ hitting the detector by additional spatial filtering optics, and thereby maximizing the efficiency of the collected light from the (fluorescently) scattering clusters. Furthermore, it potentially allows for a very compact and simple reader geometry. A disadvantage is a somewhat lower overall fluorescence cross section (absorption cross section times fluorescence quantum yield) as compared to the scattering cross section.

When an ultra-thin system as shown in FIG. 7 is desired, all components including the magnetic assembly (coils, cores, yokes) should be as much as possible in the xy-plane. When the plane of magnetic rotation is in the xy plane, then preferably the excitation light beam $L_0$ should be directed towards the sample chambers from the side, in the xy-plane. When the plane of magnetic rotation is in the xz-plane or yz-plane, then preferably excitation is used along the z-axis.

In summary, the invention provides a sensor apparatus and a method for detecting clusters with magnetic particles in a sample. The sample is provided in at least one sample chamber of a substantially planar cartridge that is exposed to a modulated magnetic field generated by a magnetic field generator. The sample chamber is illuminated with excitation light $L_0$, and the resulting output light $L_s$, $L_f$ is detected by a light detector. The magnetic field may particularly rotate, inducing a corresponding rotation of clusters which in turn induces a variation of the detection signal. According to a preferred embodiment, excitation light is focused onto blocking spots behind the sample chamber, thus shielding the light detector from direct illumination.

Preferably the magnetic actuation is chosen such that the axis of optical excitation falls in the plane of angular actuation of the particle clusters. In this geometry the clusters expose a time-modulated cross-section to the excitation light. If the clusters rotate in a different plane the principle is still valid, however the signal per cluster can be lower.

Preferably a quadrupolar electromagnet is used for magnetic actuation. When the surfaces of opposite pole tips are parallel and the cores of opposite poles are in line, then the magnetic field has a high spatial uniformity in the gap between the tips (as in Ranzoni et al., above). Alternatively, a magnet can be used with pole tips that are oriented at an angle, so as to generate a field outside the plane of the cores (cf. Janssen, X. J. A., van Reenen, A., van Ijzendoorn, L. J., de Jong, A. M., and Prins, M. W. J.: "The rotating particles probe: A new technique to measure interactions between particles and a substrate", Colloids and Surfaces A: Physicochem. Eng. Aspects 373, pp 88-93 (2011)).

During the detection, the magnetic particles can be spread out in a sample chamber. Alternatively, the particles are first moved toward an optical window of a sample chamber (e.g. by magnetic forces) and subsequently detection is performed in a detection region near an optical window.

Preferably the magnetic clusters in a sample chamber generate a signal in the detector that is essentially independent of the spatial position of a cluster in the detection region of a sample chamber. So preferably the magnetic fields, the optical excitation field, and the optical detection efficiency are quite uniform in the detection region of a sample chamber.

The collection of optical signals can be performed while the reader-versus-cartridge are mechanically static (for static imaging) or while the reader-versus-cartridge are scanning (for scanning readout). A scanning readout can be useful when the sample has a very large planar shape, e.g. in the case of many separate sample chambers or in case of one or more very large sample chambers (e.g. a sample spread over a slide).

The approach of the present invention with a planar architecture provides the following advantages:
- suitable for cost-effective cartridge mass manufacturing;
- easy mechanical insertion of cartridge into the reader;
- effective optomagnetic alignment of cartridge and reader;
- planar arrangement is compatible with the planar geometry of chip-like optical sensors;
- planar space is available for fluidic functions, e.g. for filtering, reagent release into the sample (from wet or dry state), transport to the sample chambers, etc.;
- on both sides of the planar cartridge, two half-spaces are available for the electromagnets and optical arrangements;
- if the electromagnets and optical arrangements are placed in one half-space, then the other half-space side of the cartridge is available for further fluidic functions, e.g. giving access for a pipetting robot;
- the planar architecture gives planar scalability of the system for multichamber operation, with separate optical signals being collected from separate sample chambers.

While the invention has been illustrated and described in detail in the drawings and foregoing description, such illustration and description are to be considered illustrative or exemplary and not restrictive; the invention is not limited to the disclosed embodiments. Other variations to the disclosed embodiments can be understood and effected by those skilled in the art in practicing the claimed invention, from a study of the drawings, the disclosure, and the appended claims. In the claims, the word "comprising" does not exclude other elements or steps, and the indefinite article "a" or "an" does not exclude a plurality. The mere fact that certain measures are recited in mutually different dependent claims does not indicate that a combination of these measures cannot be used to advantage. Any reference signs in the claims should not be construed as limiting the scope.

The invention claimed is:

1. A sensor apparatus for detecting clusters (C) with magnetic particles (MP) in a sample, comprising:
a substantially planar cartridge with at least one sample chamber in which the sample can be provided;
a light source configured to emit excitation light ($L_0$) into said at least one sample chamber;
a magnetic field generator and a digital data processing unit operating the magnetic field generator to generate a modulated magnetic field and a pulsed magnetic chaining field in the at least one sample chamber with the pulsed magnetic chaining field being pulsed by being periodically switched on and off at a pulse frequency in the range 0.1 Hz to 100 Hz inclusive, the digital data processing unit including a non-transitory computer readable medium storing instructions thereon to control the magnetic field generator to generate the modulated magnetic field and the pulsed magnetic field;
a light detector configured to detect output light ($L_s$, $L_f$) generated by excitation light ($L_0$) in the at least one sample chamber.

2. The sensor apparatus according to claim 1, wherein the substantially planar cartridge has x and y dimensions, respectively, in an (x,y) plane of an (x,y,z) rectangular coordinate system that are at least three times greater than a z dimension of the substantially planar cartridge, and the light detector is disposed adjacent to the plane (x,y) of the substantially planar cartridge.

3. The sensor apparatus according to claim 1,
wherein the digital data processing unit is further configured to evaluate detector signals (S) with respect to their temporal spectrum.

4. The sensor apparatus according to claim 1, wherein a nontransparent blocking spot is provided between the at least one sample chamber and the light detector onto which the excitation light ($L_0$) is focused.

5. The sensor apparatus according to claim 1, wherein an optical element is provided between the at least one sample chamber and the light detector for directing output light ($L_s$, $L_f$) onto the light detector.

6. The sensor apparatus according to claim 1, wherein a distribution element is provided for directing excitation light ($L_0$) that arrives at said distribution element parallel to a plane of the substantially planar cartridge into the at least one sample chamber.

7. The sensor apparatus according to claim 6, wherein the distribution element comprises at least one partial mirror.

8. The sensor apparatus according to claim 1, wherein the substantially planar cartridge comprises: a transparent layer in which the at least one sample chamber is formed and through which the excitation light ($L_0$) can propagate; and an additional layer adjacent to the transparent layer at which the excitation light ($L_0$) is reflected.

9. The sensor apparatus according to claim 8, wherein the additional layer comprises two layers having a lower refractive index than the transparent layer, the transparent layer being disposed between the two layers.

10. A method for detecting clusters (C) with magnetic particles (MP) in a sample, said method comprising:
    introducing the sample into at least one sample chamber of a substantially planar cartridge;
    emitting excitation light ($L_0$) into said at least one sample chamber;
    generating a modulated magnetic field and a pulsed magnetic chaining field in the at least one sample chamber with the pulsed magnetic chaining field being pulsed by being periodically switched on and off at a pulse frequency in the range 0.1 Hz to 100 Hz inclusive; and
    detecting, with a light detector, output light ($L_s$, $L_f$) that was generated by excitation light ($L_0$) in the at least one sample chamber.

11. The method according to claim 10, wherein the generating comprises:
    generating the modulated magnetic field as a rotating magnetic field that rotates in a plane containing the excitation light ($L_0$).

12. The method according to claim 10, wherein the output light ($L_s$, $L_f$) that was generated by excitation light ($L_0$) in the at least one sample chamber comprises light generated by fluorescence of clusters (C).

13. The method according to claim 12, further comprising:
    providing a filter element between the at least one sample chamber and the light detector for spectrally filtering out excitation light ($L_0$) while allowing the passage of the output light ($L_s$, $L_f$).

14. A sensor apparatus for simultaneously assaying a plurality of samples, the sensor apparatus comprising:
    a multi-assay planar cartridge with a plurality of sample chambers each comprising a cavity defined in the planar cartridge for holding a fluid sample;
    a light source configured to simultaneously emit excitation light into each sample chamber of the plurality of sample chambers;
    a magnetic field generator configured to simultaneously generate a modulated magnetic field and a pulsed magnetic field in each sample chamber of the plurality of sample chambers;
    an array of light detectors, each light detector arranged to detect output light generated by excitation light in only a corresponding one sample chamber of the plurality of sample chambers; and
    a digital data processing unit including a non-transitory computer readable medium storing instructions thereon to control the magnetic field generator to generate the modulated magnetic field and the pulsed magnetic field.

15. The sensor apparatus of claim 14 wherein the magnetic field generator is configured to generate the pulsed magnetic field in each sample chamber of the plurality of sample chambers at a pulse frequency in the range 0.1 Hz to 100 Hz inclusive.

* * * * *